US009772318B1

(12) United States Patent
Lyon

(10) Patent No.: US 9,772,318 B1
(45) Date of Patent: Sep. 26, 2017

(54) INTERLOCK DATA COLLECTION AND CALIBRATION SYSTEM

(71) Applicant: Michael Lyon, Redlands, CA (US)

(72) Inventor: Michael Lyon, Redlands, CA (US)

( * ) Notice: Subject to any disclaimer, the term of this patent is extended or adjusted under 35 U.S.C. 154(b) by 1001 days.

(21) Appl. No.: 13/955,260

(22) Filed: Jul. 31, 2013

(51) Int. Cl.
*G01F 1/12* (2006.01)
*G01N 33/00* (2006.01)

(52) U.S. Cl.
CPC ............... *G01N 33/0008* (2013.01)

(58) Field of Classification Search
CPC .................................. G01N 33/0008
USPC ......................................... 702/100
See application file for complete search history.

(56) References Cited

U.S. PATENT DOCUMENTS

| | | | |
|---|---|---|---|
| 3,780,311 A | 12/1973 | Brown | |
| 3,824,537 A | 7/1974 | Albertson | |
| 3,831,707 A | 8/1974 | Takeuchi | |
| 4,391,777 A * | 7/1983 | Hutson | G01N 33/4972 250/343 |
| 4,487,055 A | 12/1984 | Wolf | |
| 4,592,443 A | 6/1986 | Simon | |
| 4,697,666 A | 10/1987 | Collier | |
| 6,026,674 A | 2/2000 | Gammenthaler | |
| 6,167,746 B1 | 1/2001 | Gammenthaler | |
| 6,853,956 B2 | 2/2005 | Ballard, Jr. et al. | |
| 6,956,484 B2 | 10/2005 | Crespo | |
| 7,204,335 B2 | 4/2007 | Stewart et al. | |
| 7,422,723 B1 * | 9/2008 | Betsill | G01N 33/4972 422/411 |
| 8,059,003 B2 * | 11/2011 | Roth | B60K 28/063 180/272 |
| 2007/0144812 A1 * | 6/2007 | Stewart | B60K 28/063 180/272 |
| 2009/0278656 A1 * | 11/2009 | Lopez | B60R 25/24 340/5.72 |
| 2010/0012417 A1 * | 1/2010 | Walter | B60K 28/063 180/272 |
| 2010/0081909 A1 * | 4/2010 | Budiman | A61B 5/14532 600/365 |
| 2010/0108425 A1 * | 5/2010 | Crespo | A61B 5/082 180/272 |
| 2013/0282321 A1 * | 10/2013 | Son | G01N 33/0008 702/104 |
| 2014/0041436 A1 | 2/2014 | Knott et al. | |

* cited by examiner

*Primary Examiner* — Toan Le
*Assistant Examiner* — Xiuquin Sun
(74) *Attorney, Agent, or Firm* — Benjamin Diederich; Law Office of Benjamin Diederich

(57) ABSTRACT

An interlock data collection and calibration system has a device computer, a gas delivery system, and a data port. The device computer has a computer processor and a computer memory. The gas delivery system delivers a gas sample to an ignition interlock device. The data port is operably connected with the device computer for enabling sample data from the ignition interlock device to be transmitted to the device computer. A calibration program operably installed on the computer memory receives the sample data, calibrates the ignition interlock device, and generates confirmation data, which is stored in a local database.

13 Claims, 4 Drawing Sheets

INTERLOCK DATA COLLECTION AND CALIBRATION SYSTEM

BACKGROUND OF THE INVENTION

Field of the Invention

This invention relates generally to ignition interlock devices, and more particularly to a system for calibrating ignition interlock devices, and storing data related to the ignition interlock devices.

Description of Related Art

Driving under the influence of alcohol is a well known safety hazard, which causes thousands of deaths per year in the United States alone. To address this problem, states have established laws that criminalize operation of a vehicle and other machinery with a blood alcohol concentration ("BAC") greater than a preset value (e.g., 0.08% BAC).

To reduce the rate of recidivism of driving under the influence, many states require the installation of devices in the vehicles and other machinery of individuals convicted of driving under the influence of alcohol. Such devices, which are commonly referred to as breath alcohol ignition interlock devices ("IID"). These IIDs have been developed to be directly connected to a vehicle's ignition system and are designed to prevent automobiles and other machinery from being operated by inebriated individuals.

IIDs typically include semiconductor sensors, commonly referred to as a Taguchi cell, and/or fuel cells to sense and quantify the amount of alcohol in a driver's breath. Most modern IIDs use an ethanol-specific fuel cell for a sensor. Examples of these sensors are shown in U.S. Pat. No. 4,487,055, U.S. Pat. No. 6,026,674, U.S. Pat. No. 6,167,746, and/or U.S. Pat. No. 7,204,335, which are hereby incorporated by reference.

As described in the noted patents, a fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable as infrared spectroscopy technology used in evidentiary breathalyzers, they are less expensive and specifically tailored to quantify ethyl alcohol (drinking alcohol). Among manufacturers of IIDs are Smart Start Inc., LifeSafer Interlock, SOS, Ignition Interlock Systems, Intoxalock and Monitech. A list of federally-approved IID devices is maintained by the National Highway Traffic Safety Administration ("NHTSA") in its NHTSA Conforming Products List.

Typically, in order to start a vehicle equipped with an IID, the driver must first blow into the breath analyzer installed in the vehicle or machinery. Conventional IIDs measure the alcohol content of the breath and calculate BAC readings on the alcohol content of gas present in the alveoli of the lungs by approximating, through the use of software algorithms, the alcohol content in the bloodstream. If the driver's BAC exceeds a preset limit, the vehicle's ignition is disabled and the vehicle is rendered inoperable. If the driver's BAC is below the preset limit, ignition is permitted and the vehicle may be started. Exemplary ignition interlock devices that utilize breath analyzers are described in, for example, U.S. Pat. Nos. 3,780,311, 3,824,537, 3,831,707, 4,592,443, and 4,697,666.

Generally, the methods for detecting BAC and using ignition interlock systems to prevent automobiles and other machinery, from being operated by inebriated individuals are well known in the current art. Moreover, the current invention does not rely on any particular ignition interlock device or method for testing BAC, but instead can be universally applied to any ignition interlock data retrieved from any ignition interlock device installed on any vehicle or equipment.

Roth, U.S. Pat. No. 8,059,003, teaches a system and method for collecting data from IID, and uploading the data to a central server. This reference teaches the use of encryption and date stamping to provide reliable evidence regarding the use of the IID, for use in courts. The above-described references are hereby incorporated by reference in full.

SUMMARY OF THE INVENTION

The present invention teaches certain benefits in construction and use which give rise to the objectives described below.

The present invention provides an interlock data collection and calibration system for use with an ignition interlock device. The system includes a device computer having a computer processor and a computer memory; a gas delivery system to provide a calibration reference to the ignition interlock device; a data port operably connected with the device computer for enabling sample data from the ignition interlock device to be transmitted to the device computer; a calibration program operably installed on the computer memory of the device computer for receiving the sample data, calibrating the ignition interlock device, and generating confirmation data that the ignition interlock device was calibrated; and a local database operably installed on the computer memory of the device computer for storing and encrypting the confirmation data.

A primary objective of the present invention is to provide an integrated interlock data collection and calibration system having advantages not taught by the prior art.

Another objective is to provide an interlock data collection and calibration system that is able to automatically calibrate an IID in a reliable manner.

Another objective is to provide an interlock data collection and calibration system that is able to automatically gather, encrypt, and store data related to the calibration and use of the system for evidentiary purposes.

A further objective is to provide an interlock data collection and calibration system that prevents use of the IID if the IID fails calibration, or otherwise requires maintenance or replacement.

A further objective is to provide a calibration system that provides an accurate and manageable data delivery and reporting system for ignition interlock related data.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a interlock data collection and calibration system 10 ("IDCCS") for use with an ignition interlock device 12 ("IID"). The IDCCS 10 is used to calibrate the IID 12, and to receive, upload to, and store data from the IID 12 in a local database 118. The contents of the local database 118 may also be uploaded to a central database 138, as discussed in greater detail below.

Figure 1:
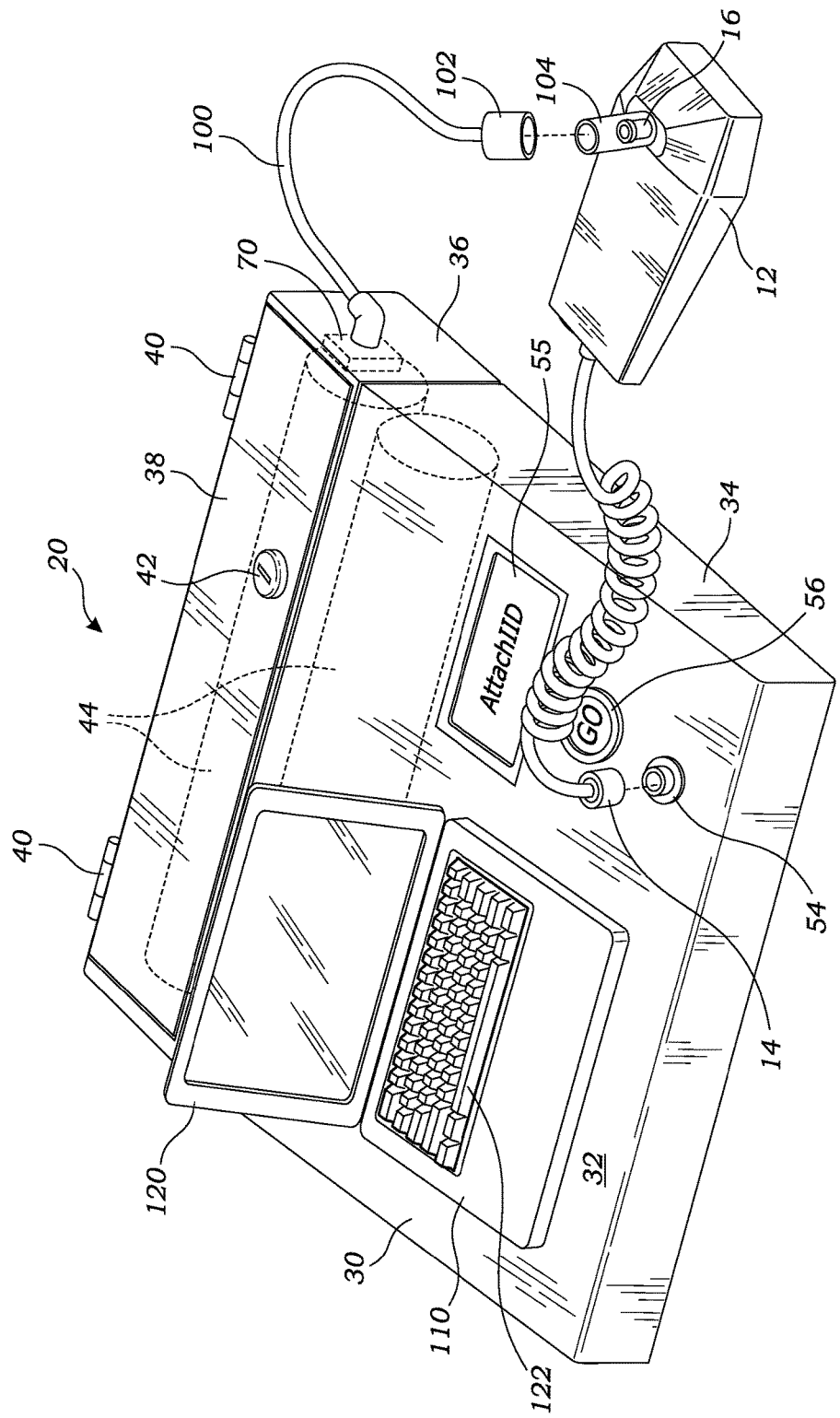
FIG. 1 is a perspective view of one embodiment of an interlock data collection and calibration system.
Figure 2:
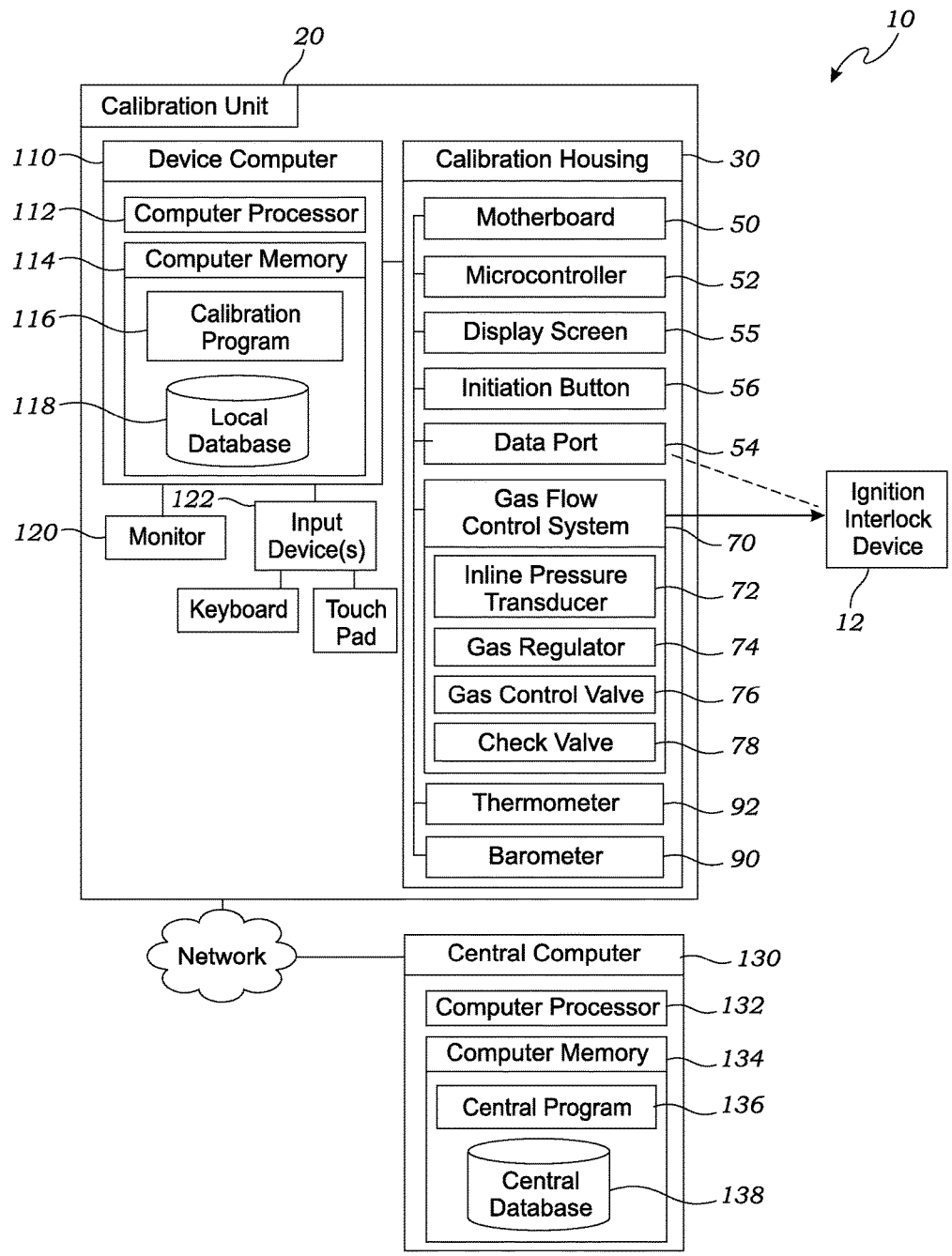
FIG. 2 is a block diagram of the interlock data collection and calibration system of FIG. 1.

FIG. 1 is a perspective view of one embodiment of the IDCCS 10. FIG. 2 is a block diagram of the IDCCS 10 of FIG. 1. As illustrated in FIGS. 1-2, the IDCCS 10 includes a calibration unit 20 that is adapted to connected with the IID 12 for calibrating the IID 12. The calibration unit 20 includes a calibration housing 30 and a device computer 110. While the calibration housing 30 and the device computer 110 are illustrated as two separate units in this embodiment, they could also be integrated into a single unit, in an alternative embodiment, wherein operable components of the device computer 110 are incorporated into the calibration housing 30.

In the embodiment of FIG. 1, the calibration housing 30 is a generally rectangular housing that is built to contain and protect the various electronic components described below. The calibration housing 30 may include a top surface 32, side walls 34, and a rear chamber 36 that includes a cover 38, attached with a hinge 40 and a latch element 42 (in this case, a lock), for covering the rear chamber 36. The rear chamber 36 is shaped to contain one or more gas cylinders 44. While one embodiment of the calibration housing 30 is illustrated, those skilled in the art may devise alternative structures, and such alternatives should be considered within the scope of the present invention.

The gas cylinder 44 installed in the calibration housing 30 is for holding a prefilled gas for use in calibrating the calibration unit 20. The gas contains a predetermined amount of alcohol, for the purposes of calibrating the IID 12. The gas cylinder 44 is connected to a gas delivery system 70 that releases the gas through the gas delivery system 70. The gas cylinder 44 in the present embodiment is shown contained within the calibration housing 30, however in an alternate embodiment it may also be attached externally, or operably connected in some other manner. Also, it is possible for the calibration housing 30 to contain multiple gas cylinders 44 so that there is a spare gas cylinder 44 readily at hand. While the gas cylinder 44 is illustrated, in an alternate embodiment this may be replaced by a "wet media" or "wet bath" system. In that embodiment, a container (not shown) contains water with ethanol or another alcohol solution dissolved at a known concentration within the water; and air is delivered at a specific flow rate through the solution to simulate the absorption of alcohol into the exhaled breath of a customer.

In the embodiment of FIGS. 1-2, the calibration housing 30 contains a motherboard 50, a microcontroller 52 connected to the motherboard 50, and a data port 54 also connected to the motherboard 50. The motherboard 50 is used to seat the microcontroller 52, and to also interconnected with the device computer 110 (or to seat the operably components thereof), as well as any integrated circuitry, computer chips, peripherals such as I/O ports and their associated devices, and any other components that may be desired. In the present embodiment the motherboard 50 is also connected to the gas delivery system 70, described in greater detail below.

The microcontroller 52 controls the interaction between other components of the calibration housing 30, such as a display screen 55, an initiation button 56, the gas delivery system 70, and the data port 54. As used in this application, the term "microcontroller" is hereby defined to include any form of processor and memory, integrated or apart, that can function to enable the operation of the IDCCS. The microcontroller 52 may also be connected to interface with an external device such as a personal computer, or any other device capable of interfacing with the calibration unit 20, via any form of wired or wireless connection known in the art.

The data port 54 is shaped and adapted for connecting the IDCCS 10 to the IID 12 to receive sample data for analysis. The data port 54 is operatively positioned on the calibration housing 30 for connection with a data plug 14 of the IID 12, either directly or via an adaptor (not shown) that enables the data port 54 to accept sample data from a wider range of IID 12 output connections. Some examples of the data port 54 types are USB, DVI, VGA, coaxial, and other equivalent ports.

The display screen 55 is used for communicating information to the user, such as device status, instructions, error codes, and/or other similar information. The display screen 55 is operatively mounted on the calibration housing 30, in this embodiment on the top surface 32, to allow the user to read the display screen 55 during use of the IDCCS 10. The display screen 55 may be any form of display known in the art (e.g., liquid crystal display, digital, or their equivalents).

Also located operatively on the calibration housing 30 is the initiation button 56 which is used to initiate a manual calibration procedure or when so directed by the device computer 110. The initiation button 56 is hereby defined to include any form of button, switch, turnkey, touchscreen, or similar/equivalent device or method of actuation known in the art. In the present embodiment, the initiation button 56 is a normally OFF button which when pressed initiates the calibration procedure and then returns to an OFF state. Other embodiments could include a button that remains in the ON state until the end of the calibration procedure or include intermediate states, such as a three-way switch if a stand-by or warm-up mode is desired.

The IDCCS 10 may also include a barometer 90 for the monitoring of the ambient air pressure. This plays a key role as the local air pressure must be taken into account when generating a prescribed concentration of alcohol vapor for use in the calibration procedure and generating blood alcohol content equivalents for calibration of the IID, as discussed in greater detail below.

In this embodiment, the IDCCS 10 may also include a thermometer 92 for measuring the local temperature, as the temperature is also a factor in getting a proper reading of the IID 12. Another reason for acquiring an accurate temperature during the calibration is that the reading of the IID 12 is temperature dependent and therefore the calibration of the IID 12 must take this into account.

As illustrated in FIGS. 1 and 2, the gas delivery system 70 is for delivering a gas sample to the IID 12 from the gas cylinder 44 stored in the calibration housing 30. The gas delivery system 70 may include, in the present embodiment, an inline pressure transducer 72, a gas regulator 74, gas control valves 76, and check valves 78. The operation of the gas delivery system 70 is controlled by the microcontroller 52. When the microcontroller 52 is given the command to open the gas control valve 76, the gas control valve 76 opens and releases gas from the gas cylinder 44, through the gas control valve 76, the gas regulator 74, the check valve 78, to the IID 12 via a sample flow tube 100. The inline pressure transducer 72 monitors the pressure in the gas cylinder 44. A low reading of the inline pressure transducer 72 could indicate a leak, faulty installation of the gas cylinder 44, or a depleted gas cylinder 44.

The inline pressure transducer 72 can consist of any analog or digital gauge capable of measuring the pressure in the gas cylinder 44 and transmitting the data to the device computer 110 for monitoring and analysis. Types of inline pressure transducers 72 that could be used include piezoresistive strain gauges, electromagnetic, or potentiometric.

The gas regulator 74 is used to reduce the gas pressure within the gas cylinder 44 to a desired pressure for use in the calibration. The gas regulator 74 may be of any type that is compatible with a step-down pressure adjustment. Also the gas regulator 74 is compatible with the gas being used, alcohol being a flammable and reactive compound in sufficiently high concentrations.

The gas control valve 76 is a valve for the control of a specified amount of gas from the gas cylinder 44 to the sample flow tube 100 or equivalent component. The gas control valve 76 is connected to the gas regulator 74. The gas control valve 76 may be of any type capable of enabling the controlled release of gas from the gas cylinder 44 for the period of time specified by the user and/or dictated by the calibration procedure. Examples of gas control valves 76 suitable for such a purpose include, but are not limited to, solenoidal valves, mechanical valves, pneumatic valves, etc. The operation of the gas control valve 76 is controlled by the microcontroller 52 mounted on the motherboard 50, which receives commands from the device computer 110 during the calibration procedure.

The check valve 78 is used to prevent the backflow of air or other gasses into the gas delivery system 70 which may cause contamination. Any form of check valve 78 or equivalent may be included, including but not limited to ball check valves, diaphragm check valves, stop-check valves, lift-check valves, in-line check valves, or other similar devices known in the art.

The sample flow tube 100 may be any form of nonreactive tube for directing the flow of gas from the gas cylinder 44 to the IID 12. The sample flow tube 100 may include a connector 102 that enables a connection to a breath receiving port 16 of the IID 12. An adaptor 102 may be provided that facilitates connecting the sample flow tube 100 to the IID 12. The sample flow tube 100 may be, for example, a flexible plastic, rubber, nylon or metal hose, or any other suitable device known in the art.

As shown in FIGS. 1-2, the device computer 110 may be any form of computer components for executing the calibration procedures described herein. In this case, for simplicity, the device computer 110 is a separate laptop computer (or, alternatively, a desktop computer, tablet computer, etc.). In another embodiment, the microcontroller 52 described above might be used, with or without other processing components, memory chips, etc. Any equivalent construction known in the art may be utilized.

Importantly, the device computer 110 has a computer processor 112 and a computer memory 114 with a calibration program 116 installed on the computer memory 114 of the device computer 110 for receiving the sample data, calibrating the IID 12, and generating confirmation data that the IID 12 was calibrated. Additionally, the calibration program 116 is capable of transmitting a calibration date and or other unique identifier to the IID 12.

In the present embodiment, the calibration program 116 transmits a new calibration date to the IID 12 only after the confirmation data has been generated following a successful calibration of the IID 12. The device computer 110 also includes a local database 118 operably installed on the computer memory 114 of the device computer 110 for storing the confirmation data. The information stored on the local database 118 includes, but is not limited to, the customer's (person being monitored by the IID 12) name, IID 12 unit serial number (both handset and vehicle blocking system), vehicle information such as year, make, model, and vehicle identification number ("VIN"), and prior test results. This information is cross-referenced with existing data in the local database for verifying the identity of the customer. In the present embodiment, the device computer 110 is a laptop computer with a monitor 120, and input devices 122 (such as a keyboard and/or touchpad) and interfaced with the calibration unit 20 to control the functions of the elements within the calibration housing 30 and manage the calibration procedure. In other embodiments the device computer 110 could be a tablet, desktop computer, mobile device, or other computer of equivalent function.

As shown in FIG. 2, the IDCCS 10 may also include a central computer 130 having a computer processor 132 and a computer memory 134. The central computer 130 has a central program 136 and a central database 138 operably installed on the computer memory 134 of the central computer 130. The central program 136 of the central computer 130 receives data from the local database 118 (or, in typical embodiments, a large number of such device computers). The data may be updated in real time, or periodically, and may be transmitted in any manner known in the art (e.g., via a direct connection, LAN, Ethernet, USB line, or over a network, where the connection may either be physical or wireless). The data is stored in the central database 138, where it can then be compiled, analyzed, or otherwise used according to the needs of one skilled in the field.

One of the primary function of the central program 136 is to analyze the data received from the calibration unit 20 to determine the state of a fuel cell or any sensor of the IID 12. For example, a systematic drift in the data received could indicate a degradation of the fuel cell sensor that could lead to erroneous readings when used by a customer. The central database 138 serves a number of functions, including backup storage of data in addition to the data stored on the local databases 118 of all connected calibration units 20, allowing cross-referencing of customer data with other data which may not be stored in the local database 118, or allowing cross-referencing of calibration data between other calibration units 20 to perform a diagnostic function or general reliability testing.

Figure 3:
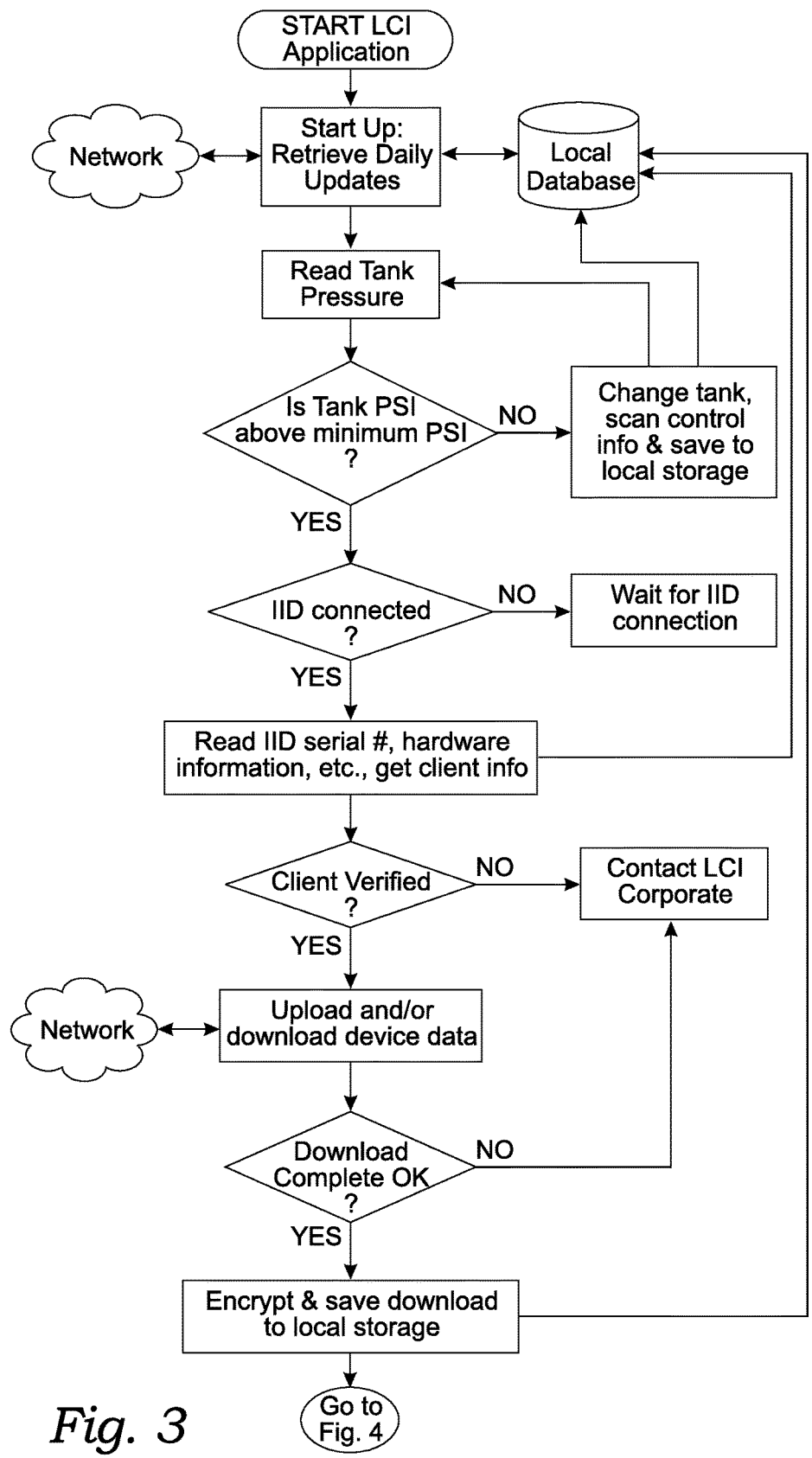
FIG. 3 is a flow diagram of a first part of the operation of the interlock data collection and calibration system of FIG. 1.
Figure 4:
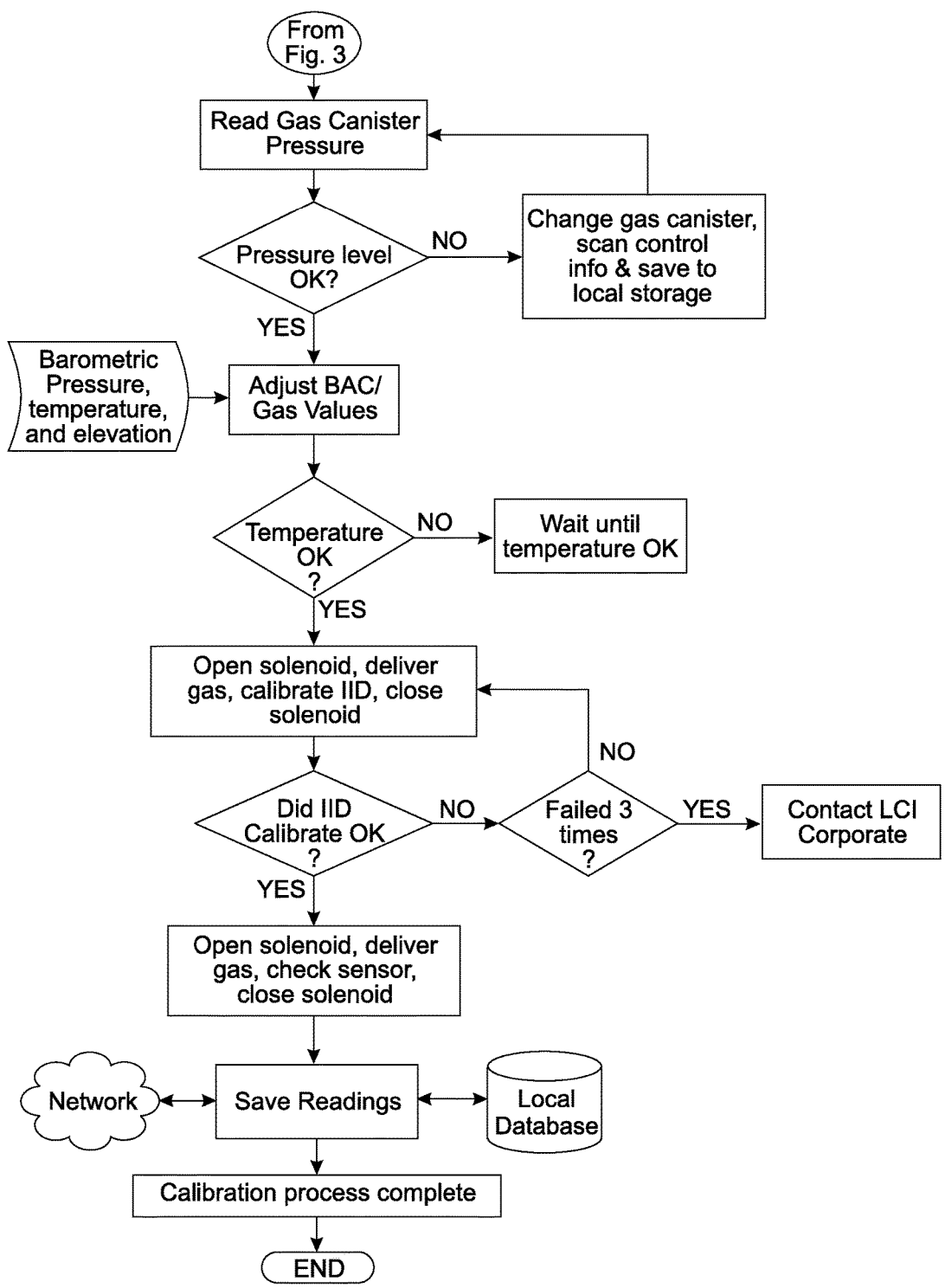
FIG. 4 is a flow diagram of a second part of the operation of the interlock data collection and calibration system.

FIGS. 3 and 4 are flow diagrams of the operation of the system of FIG. 1. As illustrated in FIGS. 3-4, the calibration procedure is initiated by starting the calibration program 116, typically either by the user pressing the initiation button 56 on the calibration housing 30 or an automatic startup when the system is powered on. This begins the startup phase, where the IDCCS 10 communicates with the network via wireless, landline, 4G internet, etc., and receives daily updates, such as software updates, database updates or other procedures. Any database updates are stored on the local database 118. Also, the IDCCS 10 may send data to and receive data from the central computer 130 such as test results, prior calibration data, or other data regarding the systems usage or status.

In this embodiment, the next step in the calibration procedure is to read the gas cylinder 44 pressure via the inline pressure transducer 72. If the gas cylinder 44 pressure is below a minimum pressure then the user is instructed to remove the low pressure gas cylinder 44, scan the bar code of a replacement gas cylinder 44 which is then stored in the local database 118 and the central database 138, and finally connect a full gas cylinder 44. The gas cylinder 44 is connected to the leak tight delivery system consisting of the inline pressure transducer 72, an optional pressure relief valve (not shown), the gas regulator 76, the gas control valve 76, and the check valve 78. The gas cylinder 44 pressure is once again determined via the inline pressure transducer 72 to confirm that the pressure is above the required minimum. Once this is satisfied, the calibration program 116 confirms that the IID 12 is connected to the data port 54. If the IID 12 is not connected, the calibration program 116 waits until this condition is satisfied before continuing with the procedure. Once the IID 12 is operably connected to the data port 54, the calibration program 116 receives the IID 12 serial number, hardware information, etc. as well as getting customer information stored on the IID 12. The calibration program 116 then verifies the client identity, for example, by cross-checking the IDCCS 10 identifiers with the IID 12 serial number, pass codes, or other identifiers. If the customers identification cannot be verified, the user is prompted to contact the central office for further instructions. Once the clients identity has been verified, device data which was recorded on the IID 12 is downloaded into the computer memory 114 of the device computer 110. An internal check is performed to confirm that the download is complete and without errors, and if incomplete or if errors are present, the user is prompted to contact the central office for further instructions. After a complete and successful download of the device data, the device data is encrypted and saved to the local database 118.

As shown in FIG. 4, the procedure from FIG. 3 continues by once again reading the gas cylinder 44 pressure via the inline pressure transducer 72. This second pressure check is performed to ensure that there are no leaks in the system or that the gas cylinder 44 is properly connected. An unexpected pressure drop could indicate a leak as well as introduce the possibility of external contamination into the gas delivery system 70 or gas cylinder 44. The second pressure check helps to avoid a faulty calibration and giving incorrect test results when the IID 12 is used. If the gas cylinder pressure is below a minimum pressure then the user is instructed to remove the low pressure gas cylinder 44, scan the bar code of a replacement gas cylinder 44 which is stored in the local database 118 and the central database 138, and finally connect a full gas cylinder 44. The gas cylinder 44 pressure is once again read via the inline pressure transducer 72 to confirm that the pressure is above the required minimum.

Once the gas cylinder 44 pressure is confirmed to be within an acceptable range, the calibration program 116 receives the local barometric pressure from the barometer 90, and receives the temperature from the thermometer 92, and adjusts the gas flow rates or concentrations, correcting for the local barometric pressure and the temperature, which may vary from location to location depending on the weather conditions and/or elevation. After correcting for the pressure and the temperature, the calibration program 116 checks to make sure that the temperature is within an acceptable range. If the temperature is not in an acceptable range, the calibration procedure will stop and the device will wait until the temperature is within the acceptable range before continuing.

The next step is to open the gas control valve 76, deliver the gas from the gas cylinder 44 to the IID 12 via the sample flow tube 100, perform the IID 12 calibration and finally close the gas control valve 76. After the IID 12 calibration is performed, a diagnostic is run to determine if the calibration was successful. If not, then the calibration is repeated up to three times, re-running the diagnostic after each attempt. In the event that there are three failures in a row, the user is prompted to contact the central office for instructions. Once the diagnostic confirms that the IID 12 has been properly calibrated, the gas control valve 76 is opened, gas is delivered to the IID 12, the sensor in the IID 12 is checked, and the gas control valve 76 is closed. All of the readings taken by the calibration program 116 are then saved to the local database 118 and a final procedure ending the calibration process is performed. At this point the calibration of the IDCCS 10 is complete and the IID 12 is ready to be used by the customer.

As used in this application, the terms computer, processor, memory, and other computer related components, are hereby expressly defined to include any arrangement of computer(s), processor(s), memory device or devices, and/or computer components, either as a single unit or operably connected and/or networked across multiple computers (or distributed computer components), to perform the functions described herein.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. An interlock data collection and calibration system for use with an ignition interlock device, the system comprising:
    a device computer having a computer processor and a computer memory;
    a gas delivery system for delivering a gas sample to the ignition interlock device, wherein the gas delivery system includes a cylinder of compressed alcohol sample gas, and a gas control valve operably installed on the cylinder and controlled by a microcontroller for releasing controlled samples of the compressed alcohol sample gas to the ignition interlock device;
    a data port operably connected with the device computer for enabling sample data from the ignition interlock device to be transmitted to the device computer;
    a calibration program operably installed on the computer memory of the device computer for receiving the sample data, calibrating the ignition interlock device, and generating confirmation data that the ignition interlock device was calibrated; and
    a local database operably installed on the computer memory of the device computer for storing the confirmation data;
    wherein the device computer is separate from and detachably connectable to the ignition interlock device via the data port, and wherein the device computer operatively controls the microcontroller of the gas delivery system responsive to the calibration program.

2. The interlock data collection and calibration system of claim 1, wherein the local database includes a user identifier stored in conjunction with the confirmation data.

3. The interlock data collection and calibration system of claim 2, wherein the local database further includes customer data, vehicle data and test data, stored in conjunction with the confirmation data.

4. The interlock data collection and calibration system of claim 1, further comprising a calibration housing that contains a motherboard that is operably connected with a microcontroller, the gas delivery system, and the data port.

5. The interlock data collection and calibration system of claim 1, wherein the calibration program transmits a new calibration date to the ignition interlock device only after the confirmation data has been generated following a successful calibration of the ignition interlock device.

6. The interlock data collection and calibration system of claim 1, further comprising a central computer having a computer processor and a computer memory, the central computer having a central program and a central database operably installed on the computer memory.

7. The interlock data collection and calibration system of claim 6, wherein the central program receives data from the local database and stores the data in the central database.

8. The interlock data collection and calibration system of claim 7, wherein the central program analyzes the data in the central database to determine a state of a fuel cell or any sensor of the ignition interlock device.

9. The interlock data collection and calibration system of claim 1, wherein the device computer includes a display screen operably connected with the device computer for displaying system status or other information.

10. The interlock data collection and calibration system of claim 1, wherein the interlock data and calibration system includes an initiation button operably connected with the device computer for initiating the calibration procedure.

11. The interlock data collection and calibration system of claim 1, wherein the interlock data and calibration system further includes a thermometer for monitoring the ambient temperature of the gas delivery system.

12. The interlock data collection and calibration system of claim 1, wherein the gas delivery system further comprises an inline pressure transducer operably connected to the gas cylinder, a gas regulator connected to the inline pressure transducer and operably controlled by the device computer, a gas regulator connected to the inline pressure transducer and controlled by the microcontroller, a gas control valve operably installed on the gas regulator and controlled by the microcontroller, a check valve connected to the gas control valve, a sample flow tube connected to the check valve, and an adaptor connected to the sample flow tube.

13. The interlock data collection and calibration system of claim 1, wherein the gas delivery system includes a pressure relief valve operatively connected to the gas cylinder.

* * * * *